United States Patent [19]

Agusti

[11] 4,107,161
[45] Aug. 15, 1978

[54] BIS(TRIAMCINOLONE ACETONIDE)-4,4'-METHYLENEBIS-(3-METHOXY-2-NAPHTHOATE)

[75] Inventor: Agustín Agusti, Barcelona, Spain

[73] Assignee: J. Uriach & Cia. S.A., Barcelona, Spain

[21] Appl. No.: 452,322

[22] Filed: Mar. 18, 1974

[51] Int. Cl.² .............................................. C07J 71/00
[52] U.S. Cl. ............................. 260/239.55 D; 424/241
[58] Field of Search ................................ 260/239.55 D

[56] References Cited

FOREIGN PATENT DOCUMENTS 889,766  2/1962  United Kingdom ........... 260/239.55 D Primary Examiner—Elbert L. Roberts
Attorney, Agent, or Firm—Michael J. Striker

[57] ABSTRACT

Bis(triamcinolone acetonide) 4,4'-methylene-bis(3-methoxy-2-naphthoate), method of preparing the same by preparing a reactive derivative of 4,4'-methylene-bis(3-methoxy-2-naphthoic acid) and reacting such derivative with triamcinoline acetonide. The triamcinolone acetonide derivative is particularly suitable for use in the treatment of dermatosis, eczema, neurodermatitis, impetigo, psoriasis, pruritis, erythema and the like.

5 Claims, No Drawings

BIS(TRIAMCINOLONE ACETONIDE)-4,4'-METHYLENEBIS-(3-METHOXY-2-NAPHTHOATE)

This invention relates to a new triamcinolone acetonide derivative, and methods for making and using the same. More particularly the invention relates to bis(triamcinolone acetonide) 4,4'-methylene-bis(3-methoxy-2-naphthoate) and the use thereof in treating a broad range of dermatological conditions.

It is well known that triamcinolone acetonide, or 9α-fluoro-11β,21-dihydroxy-16α,17α-isopropylidenedioxy-1,4pregnadiene-3,20-dione, has proved particularly useful in the treatment of dermatological conditions. The compound has been proved to have marked efficacy in the treatment of dermatosis, eczema, neurodermitis, impetigo, psoriasis, pruritis and other related diseases. However, in the long term topical treatment of large areas, especially with children and where there are skin lesions, there arise a great variety of general secondary reactions due to the percutaneous absorption of the corticoid. Thus the drug is known to induce natriuresis negative sodium balance with weight loss in most patients. Nearly every side effect seen with hydrocortisone has been seen with triamcinolone acetonide but the relative frequencies are less. These undesirable results are particularly associated with long therapy.

Triamcinolone acetonide is a fluorinated derivative of prednisone, the fluorine atom in the 9α position of the corticosteroid ring system increasing the activity of the glucocorticoid and reducing the action on the metabolism of electrolytes.

Triamcinolone acetonide is the cyclic 16,17-acetal of triamcinolone with acetone and has the following formula:

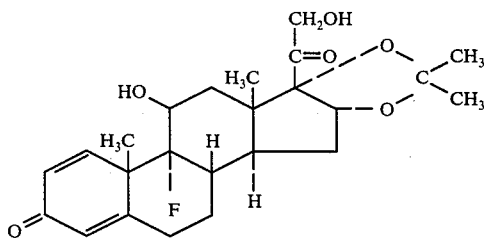

The compound of the above formula is prepared by reacting triamcinolone (9-fluoro-11β,16α, 17,21-tetrahydroxypregna-1,4-diene-3,20-dione) with acetone and perchloric acid followed by neutralization and vacuum concentration.

Triamcinolone can be synthesized from hydrocortisone acetate via the 3,20-bis ketal by treatment with thionyl chloride, refluxing with potassium hydroxide and acetylation to give 21-acetoxy-4,9,11(16)-pregnatriene-3,20-dione. Oxidation with osmium tetroxide to the 16α,17α-dihydroxy derivative and subsequent insertion of the 9α-fluoro and 11β-hydroxy groups for instance by treatment with N-bromoacetamide and perchloric acid to give the 9α-bromo-11β-hydroxy compound followed by abstraction of HBr with potassium acetate to form the 9β,11β-epoxy derivative which by treatment with HF in a halogenated hydrocarbon yields the 9β-fluoro-11β-hydroxy analog, gives a product lacking only a double bond at the 1-position. This latter step is accomplished by incubation with Norcardia corallina followed by saponification of the acetate to yield triamcinolone.

In United Kingdom patent application No. 38795/71 (now United Kingdom Pat. No. 1,332,058) a method has been described whereby the undesirable side effects of prednisone may be decreased or avoided by reacting the prednisone with an acid (particularly with an acid chloride) to form an ester which has decreased or zero absorption with respect to prednisone. The new ester has the desired anti-inflammatory properties of prednisone but may be administered without side effects resulting from absorption when given topically, orally or by injection i.e., intramuscular or intravenous routes. The acid with which the prednisone is reacted is 4,4'-methylenebis(3-methoxy-2-naphthoic acid).

The preparation of the just-mentioned acid has been described in Spanish patent application No. 385,254.

In accordance with the invention it has now been found that bis(triamcinolone acetonide)4,4-methylenebis(3-methoxy-2-naphthoate) which is a new compound is suitable for use in dermatological application. It is intended for local application, in which circumstances it is more efficaceous than triamcinolone and triamcinolone acetonide and is more potent. It is particularly adapted for use in the treatment of allergic and inflammatory dermatoses, pruritis, arthritis, bursitis, tendinitis and synovitis.

The naphthoate of the invention may be made by preparing a reactive derivative of 4,4'-methylenebis(3-methoxy-2-naphthoic acid) and thereafter reacting the derivative with triamcinolone acetonide.

In the preparation of the reactive derivative of 4,4'-methylenebis(3-methoxy-2-naphthoic acid), the acid is preferably reacted with a halogenating agent such as thionyl chloride to form two acid halide moieties on the molecule i.e.

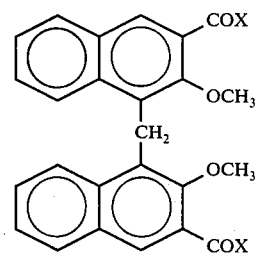

where X is halogen and preferably chlorine. This reaction should be carried out in an anhydrous medium.

The acid halide thus obtained is then reacted with triamcinolone acetonide, the preparation of which is carried out in the known manner, for instance as described above in the presence of an agent for fixing the hydracid which is formed during the reaction, so as to obtain the final product, corresponding to the formula:

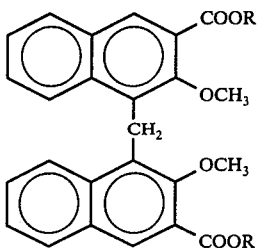

where R is the radical of triamcinolone acetonide.

As hydracid fixation agent, an organic base may be used. An example of a particularly suitable base is pyridine, which acts both as base and as a solvent for the reaction.

The following Example is given in order to illustrate the invention but is in nowise to be construed as limitative thereof.

EXAMPLE 15 grams of 4,4'-methylenebis(3-methoxy-2-naphthoic acid) were mixed with 55 ml of thionyl chloride. The resultant mixture was heated on a water bath for 2 hours, after which the excess of thionyl chloride was distilled off until a solid was obtained. The solid was purified by recrystallization from anhydrous benzene. 4,4'-Methylene-bis(3-methoxy-2-naphthoic acid) chloride was thusly obtained in the form of a yellow solid material.

Melting point: 170°–173° C
Yield: 95%
Elementary Analysis: Calculated: C = 66.23%, H = 4.02%, Cl = 15.64%; Found: C = 66.80%, H = 4.10%, Cl = 15.66%.

Ten (10) grams of the acid chloride were treated with 19.2 grams of triamcinolone acetonide in 150 ml pyridine. The mixture was heated for 3 hours at 90° C and the resultant solution added to 3 liters water. The product thus formed was recovered by filtration and was then washed with water. It was then vacuum dried at between 40° and 50° C. Bis(triamcinolone acetonide)4,4'-methylenebis(3-methoxy-2-naphthoate) was obtained in 90% yield.

After recrystallization from a mixture of acetone and water the product was found to have the following properties:

Melting point: 220° C (decomposition)
Elementary Analysis: Calculated: C = 70.18%, H = 6.29%, F = 3.04%; Found: C = 69.5%, H = 6.25%, F = 3.08%.

Clinical tests have established that the product was absorbed neither orally nor topically (even over large skin areas). In particular it was discovered that oral administration of the product did not alter the urinary excretion rates of 17-ketosteroids, sodium or potassium ions, whereas these values changed significantly when related corticoids were administered in the same dosages and under the same conditions.

However, other evaluating methods showed that the product of the invention had the same anti-flammatory activity as triamcinolone acetonide and was about 200 times as active as prednisone.

The compound may be administered in any suitable form together with a pharmaceutically acceptable carrier. For example, for topical application, it may suitably be made up in a concentration of 0.1 to 0.5% and preferably of 0.3% in the form of a cream or pomade. When the cream is applied three times daily in the conventional manner to affected areas, substantially total healing was reported in 100% of cases having various dermatological diseases as for instance contact dermatits and related allergies, eczema of physical, chemical and medical origin, flexural and housewive's eczema, impetigo, psoriasis and erythema, without any danger of secondary complaints caused by absorption of the active material.

The lack of absorption provides a further advantage of the compound, namely that there is no danger of overdosages when the medicament is applied to the skin or mucosa, or even from occlusive dressings applied directly onto affected areas.

The compound can be applied topically as a 0.1% solution, lotion, or aerosol or as a 0.1 to 0.5% cream applied 2 or 3 times daily. The compound can be administered intrasynovially, 2.5 to 15 mg as a 1% suspension at intervals of 1 to several weeks. Orally the compound is administered in amounts of 2 to 10 mg 3 to 4 times daily.

The lotion is made up in a suitable aqueous vehicle. The ointment is made up in a suitable hydrophilic ointment base. The suspension is a sterile suspension in a suitable aqueous medium.

An example of a hydrophilic base is hydrophilic petrolatum:

| | |
|---|---|
| Cholesterol | 30 grams |
| Stearyl alcohol | 30 grams |
| White wax | 80 grams |
| White petrolatum | 860 grams |
| to make | 1000 grams |

Another hydrophilic ointment base has the following composition:

| | |
|---|---|
| Methylparaben | 0.25 grams |
| Propylparaben | 0.15 grams |
| Sodium laurylsulfate | 10.00 grams |
| Propylene glycol | 120.00 grams |
| Stearyl alcohol | 250.00 grams |
| White petrolatum | 250.00 grams |
| Purified water | 370.00 grams |
| to make | 1000 grams |

The preparations, lotions, ointments or otherwise may further contain anesthetics, antiseptics, germicides, protective or screening agents, pigments, etc.

I claim:

1. Bis(triamcinolone acetonide)4,4'-methylene-bis(3-methoxy-2-naphthoate).

2. A process for the preparation of the compound of claim 1 comprising preparing a halide of 4,4'-methylenebis(3-methoxy-2-naphthoic acid) and reacting the said halide with triamcinolone acetonide in the presence of an agent for fixing the hydrogen halide that is formed during the reaction.

3. A process according to claim 2 in which the halide is the chloride.

4. A process according to claim 2 in which the agent for fixing the hydrogen halide is an organic base.

5. A process according to claim 4 in which the organic base is pyridine.

* * * * *